United States Patent
Yang et al.

(10) Patent No.: US 10,894,247 B2
(45) Date of Patent: Jan. 19, 2021

(54) FLUIDIZED-BED CATALYST SUITABLE FOR THE PRODUCTION OF HALOGENATED AROMATIC NITRILES, ITS PREPARATION AND APPLICATION THEREOF

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Weimin Yang, Shanghai (CN); Longqin Gu, Shanghai (CN); Wei Zeng, Shanghai (CN); Liang Chen, Shanghai (CN); Junfeng Xu, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 0 days.

(21) Appl. No.: 16/624,945

(22) PCT Filed: Jun. 27, 2018

(86) PCT No.: PCT/CN2018/093041
§ 371 (c)(1),
(2) Date: Dec. 20, 2019

(87) PCT Pub. No.: WO2019/007239
PCT Pub. Date: Jan. 10, 2019

(65) Prior Publication Data
US 2020/0139356 A1   May 7, 2020

(30) Foreign Application Priority Data
Jul. 3, 2017   (CN) .......................... 2017 1 0531530

(51) Int. Cl.
*B01J 29/70*  (2006.01)
*B01J 6/00*   (2006.01)
*B01J 37/00*  (2006.01)
*B01J 37/04*  (2006.01)

(52) U.S. Cl.
CPC ............... *B01J 29/70* (2013.01); *B01J 6/001* (2013.01); *B01J 37/0045* (2013.01); *B01J 37/04* (2013.01)

(58) Field of Classification Search
None
See application file for complete search history.

(56) References Cited

FOREIGN PATENT DOCUMENTS

| | | |
|---|---|---|
| CN | 1230464 A | 10/1999 |
| CN | 1230465 A | 10/1999 |
| CN | 1490080 A | 4/2004 |
| CN | 1187320 C | 2/2005 |
| CN | 1223579 C | 10/2005 |
| CN | 1252043 C | 4/2006 |
| CN | 106268890 A | 1/2017 |
| CN | 106362760 A | 2/2017 |
| CN | 107413372 A | 12/2017 |
| EP | 0525367 A1 | 2/1993 |

OTHER PUBLICATIONS

International Search Report (PCT/ISA/210) and an English translation thereof, and Written Opinion (PCT/ISA/237) dated Sep. 10, 2018, by the State Intellectual Property Office of P.R. China as the International Searching Authority for International Application No. PCT/CN2018/093041.
Office Action dated Aug. 28, 2019, by the State Intellectual Property Office of People's Republic of China in corresponding Chinese Patent Application No. 201710531530.2. (4 pages).

*Primary Examiner* — Joseph R Kosack
(74) *Attorney, Agent, or Firm* — Buchanan Ingersoll & Rooney PC (57) ABSTRACT

A fluidized-bed catalyst suitable for the production of halogenated aromatic nitriles includes an active component and a support. The active component is a complex having the following composition expressed in atomic ratio:

$VP_aCr_bA_cM_dO_x$, wherein A represents at least one metal selected from the group consisting of alkali metals and alkaline earth metals; M represents at least one element selected from the group consisting of Ti, Zr, Hf, La, Ce, Nb, Mo, W, Co, Zn, Fe, Ni, B, Sb, Bi, As, Ga, Ge, Sn, and In; in the XRD spectrum of the catalyst, diffraction peaks are present at $2\theta=27.8\pm0.5°$ and $2\theta=13.8\pm0.5°$, and the ratio of the height ($I_1$) of the diffraction peak at $2\theta=27.8\pm0.5°$ to the height ($I_2$) of the diffraction peak at $2\theta=13.8\pm0.5°$ is 3.5-6, i.e. $I_1:I_2=3.5-6$.

23 Claims, 2 Drawing Sheets

FLUIDIZED-BED CATALYST SUITABLE FOR THE PRODUCTION OF HALOGENATED AROMATIC NITRILES, ITS PREPARATION AND APPLICATION THEREOF

TECHNICAL FIELD

The present application relates to a catalyst suitable for being used as a fluidized-bed catalyst for the production of halogenated aromatic nitriles, its preparation and application thereof.

BACKGROUND ART

Halogenated aromatic nitriles are an important class of aromatic nitrile compounds, can be used in the production of medicines, pesticides, dyes and the like, and are important fine chemicals. For example, o-chlorobenzonitrile can be used to prepare the important intermediate 2-cyano-4-nitroaniline for the multipurpose azo disperse dye via nitration and ammonolysis reaction; to prepare biphenyl compounds useful in the production of non-peptide angiotensin by reacting with a halogenated benzene, and to prepare various anti-inflammatory and antibacterial drugs; and p-chlorobenzonitrile and p-bromobenzonitrile are also commonly used as intermediates for medicines and pesticides, etc.

Aromatic nitriles can be prepared using methods such as chemical synthesis, gas phase ammoxidation and the like, wherein an aromatic hydrocarbon, ammonia and air are subjected to gas phase ammoxidation to obtain an aromatic nitrile in one step, which method has a short process and less pollution, and thus is the main method for the production of aromatic nitriles at present. The reaction is characterized in that both the main and the side reactions are strong exothermic reactions. Thus, the selection of the active components and the form of the catalyst and the selection of the corresponding reactor are of great importance. Fluidized beds have the advantages of high heat and mass transfer efficiency, easiness of enlargement and the like, and also have higher requirements on the physical and chemical properties of the catalyst and the fluidization quality control in the reactor, particularly on the catalyst. Halogenated aromatic nitriles, as one class of aromatic nitriles, also meet the above characteristics.

Among fluidized-bed catalysts for preparing aromatic nitriles by ammoxidation of aromatic hydrocarbons, vanadium oxide-based catalysts are the most effective catalytic systems, such as V—P, V—Cr catalytic systems etc., and alumina, silicon carbide and silica are usually used as supports to prepare spherical particles with different particle sizes for application in a fluidized bed reactor. Early catalysts used are generally catalysts comprising oxide systems with simple compositions such as V—P—O, V—Cr—O, and generally have the problem of low selectivity of aromatic nitriles. In recent years, multi-component vanadium oxide-based catalysts are the most commonly used fluidized-bed catalysts for the production of aromatic nitriles, so that the selectivity of the aromatic nitrile is improved to a certain extent. However, most catalysts for the production of aromatic nitriles have been developed for aromatic nitrile compounds such as isophthalonitrile and terephthalonitrile, and few catalysts are developed for halogenated aromatic nitriles.

Chinese patent CN1187320C discloses a fluidized-bed catalyst for preparing o-chlorobenzonitrile, which is composed of $VCr_aB_bX_cY_dZ_eO_m/SiO_2$; Chinese patent CN1223579C discloses a fluidized-bed catalyst for preparing p-chlorobenzonitrile, which is composed of $VCr_aA_bB_cC_dO_x/SiO_2$; Chinese patent CN1252043C discloses a method for preparing p-bromobenzonitrile, which uses a supported catalyst comprising an active component of $VCr_aA_bB_cC_dO_x$. However, all the catalysts disclosed in the above three patents show better performance only for a specific halogenated aromatic nitrile product, while the applicability thereof to other halogenated aromatic nitriles is not reported.

The above fluidized-bed catalysts all use V—Cr based oxides, and a plurality of components and a silica support are added thereto at the same time, to realize the production of halogenated aromatic nitriles. However, due to the inherent structural characteristics of halogenated aromatic hydrocarbons, the presence of halo groups in the molecule makes it more difficult to activate the C—H bond at the a position, as compared to aromatic hydrocarbons such as toluene and xylene, and thus the demand for activation capability of the catalyst during ammoxidation of halogenated aromatic hydrocarbons is higher. All the catalysts reported in the above documents generally have the problem of low catalytic activity for ammoxidation of halogenated aromatic hydrocarbons. Meanwhile, if the temperature is raised or the V content in the catalyst is increased for the purpose of increasing the activity, the selectivity of the catalyst will be significantly reduced. Further improvement of the activity and selectivity for the production of halogenated aromatic nitriles is an important issue for catalyst improvement.

Chinese patent application publication CN1230464A discloses a fluidized-bed catalyst suitable for the production of 2,6-dichlorobenzonitrile, which has the composition of $V_{1.0}P_bNa_cA_dB_eO_x/SiO_2$. Chinese patent application publication CN1230465A discloses a fluidized-bed catalyst suitable for the production of 2,6-dichlorobenzonitrile and o-chlorobenzonitrile, which has the composition of $V_{1.0}P_aCr_bMo_cO_x/SiO_2$. However, both of the catalysts disclosed in these two documents require the addition of a hazardous chemical bromoethane to the raw materials of the reaction in order to obtain a high reaction conversion and selectivity.

SUMMARY OF THE INVENTION

The present application aims to overcome the problems of lower ammoxidation activity for halogenated aromatic hydrocarbons and/or lower selectivity for aromatic nitriles of catalysts in the prior art, and provide a novel catalyst suitable for the production of halogenated aromatic nitriles by ammoxidation of aromatic hydrocarbons, its preparation and application thereof. The catalyst shows a high activity and selectivity when used in the production of halogenated aromatic nitriles, is suitable for fluidized bed operation, and is more environment-friendly and relatively low in cost.

In order to achieve the above object, in an aspect, the present application provides a catalyst suitable for use as a fluidized-bed catalyst for the production of halogenated aromatic nitriles, the catalyst comprising an active component and a support, the active component being a complex having the following composition expressed in atomic ratio:

$$VP_aCr_bA_cM_dO_x$$

wherein:

A represents at least one metal selected from the group consisting of alkali metals and alkaline earth metals;

M represents at least one element selected from the group consisting of Ti, Zr, Hf, La, Ce, Nb, Mo, W, Co, Zn, Fe, Ni, B, Sb, Bi, As, Ga, Ge, Sn and In;

a is in a range of 0-1.5;
b is in a range of 0.1-1;
c is in a range of 0-0.5;
d is in a range of 0-1;
x is the number of oxygen atoms required to satisfy the valence of each element in the active component;
the support being selected from the group consisting of silica and molecular sieves,
wherein in the XRD spectrum of the catalyst, diffraction peaks are present at 2θ=27.8±0.5° and 2θ=13.8±0.5°, and a ratio of the height ($I_1$) of the diffraction peak at 2θ=27.8±0.5° to the height ($I_2$) of the diffraction peak at 2θ=13.8±0.5°, i.e. $I_1:I_2$, is in a range of 3.5-6.

In a preferred embodiment, the support is a pure-silica molecular sieve.

In another preferred embodiment, the support is a composite support composed of a pure-silica molecular sieve and silica.

In another aspect, the present application provides A method for the preparation of a catalyst suitable for use as a fluidized-bed catalyst for the production of halogenated aromatic nitriles, the catalyst comprising an active component and a support, the active component being a complex having the following composition expressed in atomic ratio:

$$VP_aCr_bA_cM_dO_x$$

wherein:

A represents at least one metal selected from the group consisting of alkali metals and alkaline earth metals;

M represents at least one element selected from the group consisting of Ti, Zr, Hf, La, Ce, Nb, Mo, W, Co, Zn, Fe, Ni, B, Sb, Bi, As, Ga, Ge, Sn and In;

a is in a range of 0-1.5;
b is in a range of 0.1-1;
c is in a range of 0-0.5;
d is in a range of 0-1;
x is the number of oxygen atoms required to satisfy the valence of each element in the active component;
the support being selected from the group consisting of silica and molecular sieves, the method comprising the steps of:

1) dissolving a vanadium-containing raw material and a chromium-containing raw material in an acid, and mixing the resultant with a solution of a M-containing raw material to obtain a first mixed solution;

2) mixing and reacting a phosphorus-containing raw material, water and a support to obtain a second mixed solution;

3) combining the first mixed solution with the second mixed solution and subjecting the resultant to concentration to obtain a mixed slurry; and 4) drying and calcining the mixed slurry to obtain the final catalyst.

In a preferred embodiment, the method comprises the steps of:

1) dissolving an amount of the vanadium-containing raw material and the chromium-containing raw material in a heated acid solution, adding thereto the promoting element-containing raw material(s) other than the phosphorus-containing raw material, respectively, heating and stirring to obtain the first mixed solution;

2) adding the support into an aqueous phosphoric acid solution, and fully heating and stirring to obtain the second mixed solution;

3) slowly adding the first mixed solution to the second mixed solution, stirring and subjecting the resultant to concentration to obtain the mixed slurry with a certain solid content; and 4) drying and molding the mixed slurry to obtain a catalyst precursor, and calcining the catalyst precursor to obtain the final catalyst.

In a further preferred embodiment, the catalyst precursor obtained in the step 4) is pre-calcined at a temperature of 300-350° C., and then calcined and activated at a temperature of 500-700° C. to obtain the final catalyst.

In yet another aspect, the present application provides a catalyst obtained by the method according to the present application.

In a further aspect, the present application provides the use of a catalyst according to the present application or a catalyst obtained by the method according to the present application as a fluidized-bed catalyst for the production of halogenated aromatic nitriles.

In a further aspect, the present application provides a process for the production of halogenated aromatic nitriles, comprising the step of contacting and reacting a halogenated aromatic hydrocarbon with a catalyst according to the present application or a catalyst obtained by the method according to the present application.

In a preferred embodiment, the contacting and reacting are carried out in the absence of bromoethane.

The catalyst according to the present application and the catalyst obtained by the method according to the present application have specific peaks in the XRD spectrum, thereby showing an excellent ammoxidation activity, and can provide a higher reaction conversion and selectivity in the absence of the dangerous chemical bromoethane when used in the preparation of halogenated aromatic nitriles, and thus is particularly suitable for industrial application. Particularly, when a pure-silica mesoporous molecular sieve is used as the support, the ammoxidation activity for halogenated aromatic hydrocarbons can be further remarkably improved, and when a composite support composed of a pure-silica molecular sieve and silica is used, the selectivity of the target product can be further remarkably improved. In addition, the catalyst according to the present application can be widely used in the ammoxidation of various halogenated aromatic hydrocarbons.

Other characteristics and advantages of the present application will be described hereinafter in detail in the Detailed Description section.

BRIEF DESCRIPTION OF THE DRAWINGS

The drawings, forming a part of the present description, are provided to help the understanding of the present application, and should not be considered to be limiting. The present application can be interpreted with reference to the drawings in combination with the detailed description hereinbelow. In the drawings.

DETAILED DESCRIPTION OF THE INVENTION

The present application will be further described hereinafter in detail with reference to specific embodiments thereof. It should be noted that the specific embodiments of the present application are provided for illustration purpose only, and are not intended to be limiting in any manner.

Any specific numerical value, including the endpoints of a numerical range, described in the context of the present application is not restricted to the exact value thereof, but should be interpreted to further encompass all values close to said exact value, i.e. be modified by the term "about". Moreover, regarding any numerical range described herein, arbitrary combinations can be made between the endpoints of the range, between each endpoint and any specific value within the range, or between any two specific values within the range, to provide one or more new numerical range(s), where said new numerical range(s) should also be deemed to have been specifically described in the present application.

In a first aspect, the present application provides a catalyst suitable for use as a fluidized-bed catalyst for the production of halogenated aromatic nitriles, the catalyst comprising an active component and a support, the active component being a complex having the following composition expressed in atomic ratio:

$$VP_aCr_bA_cM_dO_x$$

wherein:

A represents at least one metal selected from the group consisting of alkali metals and alkaline earth metals, preferably at least one selected from the group consisting of alkali metals;

M represents at least one element selected from the group consisting of Ti, Zr, Hf, La, Ce, Nb, Mo, W, Co, Zn, Fe, Ni, B, Sb, Bi, As, Ga, Ge, Sn and In;

a is in a range of 0-1.5;

b is in a range of 0.1-1;

c is in a range of 0-0.5;

d is in a range of 0-1;

x is the number of oxygen atoms required to satisfy the valence of each element in the active component;

the support being selected from the group consisting of silica and molecular sieves, wherein in the XRD spectrum of the catalyst, diffraction peaks are present at 2θ=27.8±0.5° and 2θ=13.8±0.5°, and a ratio of the height ($I_1$) of the diffraction peak at 2θ=27.8±0.5° to the height ($I_2$) of the diffraction peak at 2θ=13.8±0.5°, i.e. $I_1:I_2$, is in a range of 3.5-6, preferably in a range of 3.5-5.

In a preferred embodiment, in the composition of the composite, a is not 0; more preferably in a range from 0.5 to 1.5; even more preferably in a range from 0.5 to 1.0.

In a preferred embodiment, b is in a range from 0.1 to 0.7, more preferably in a range from 0.1 to 0.6.

In a preferred embodiment, c is in a range from 0.01 to 0.5, more preferably in a range from 0.01 to 0.3, and even more preferably in a range from 0.01 to 0.2.

In a preferred embodiment, d is in a range from 0.01 to 0.5.

In a further preferred embodiment, a is in a range from 0.5 to 1.5 and c is in a range from 0.01 to 0.5. More preferably, a is in a range from 0.5 to 1, b is in a range from 0.1 to 0.7, c is in a range from 0.01 to 0.3, and d is in a range from 0.01 to 0.5.

In a preferred embodiment, a is at least one of Na, K and Ca, more preferably at least one of K and Ca, and most preferably K.

In a preferred embodiment, M is at least one selected from the group consisting of Ti, Nb, Mo, W, Co, Zn, Fe, Ni, B, Sb, Bi and Sn, more preferably at least one selected from the group consisting of Mo, Nb, B and W.

In certain preferred embodiments, the active component of the catalyst may further comprise Se and/or Te in a molar ratio to V ranging from 0.01 to 0.2, preferably from 0.02 to 0.1.

In a preferred embodiment, the support is present in the catalyst in an amount ranging from 20% to 70% by weight, more preferably from 30% to 60% by weight.

In a preferred embodiment, the support in the catalyst according to the present application is a molecular sieve material, as opposed to conventional ammoxidation catalysts for halogenated aromatic hydrocarbons. Further preferably, the support is a pure-silica molecular sieve. Particularly preferably, the pure-silica molecular sieve is one or more selected from the group consisting of MCM-41, MCM-48, SBA-1, SBA-2, SBA-15, SBA-16, MSU, Silicate-1, SSZ-13 and HMS, most preferably SSZ-13 molecular sieve.

In certain preferred embodiments, the support in the catalyst according to the present application is a composite support composed of a pure-silica molecular sieve and silica, wherein the weight ratio of the pure-silica molecular sieve to silica is in a range from 1:9 to 9:1, more preferably from 1:4 to 4:1. Further preferably, the pure-silica molecular sieve in the composite support is one or more selected from the group consisting of MCM-41, MCM-48, SBA-1, SBA-2, SBA-15, SBA-16, MSU, Silicate-1, SSZ-13 and HMS. Particularly preferably, the support is a composite support of SSZ-13 molecular sieve and silica, and the weight ratio of the SSZ-13 molecular sieve to silica in the composite support is preferably in a range from 1:9 to 9:1, and more preferably from 1:4 to 4:1.

The catalyst according to the present application can form a complex phase structure, and the composition of the crystalline phase can be detected and defined using the X-ray diffraction (XRD) technology. The catalyst according to the present application has a $CrVO_4$ phase, and shows particularly good catalytic performance when the ratio of the height ($I_1$) of the diffraction peak at 2θ=27.8±0.50 to the height ($I_2$) of the diffraction peak at 2θ=13.8±0.5°, i.e. $I_1:I_2$, is in a range of 3.5-6, preferably 3.5-5.

In a preferred embodiment, the XRD spectrum of the catalyst according to the present application shows a ratio of the intensity of the main characteristic peak ascribed to $V_2O_5$ or $Cr_2O_3$ to the intensity of the main characteristic peak ascribed to $CrVO_4$ in a range from 0 to 0.5, wherein the "main characteristic peak ascribed to $V_2O_5$ or $Cr_2O_3$" refers to the highest peak among the characteristic peaks ascribed to $V_2O_5$ or $Cr_2O_3$ in the XRD spectrum, and the "main characteristic peak ascribed to $CrVO_4$" refers to the highest peak among the characteristic peaks ascribed to $CrVO_4$, and the ratio of the intensities of the characteristic peaks refers to the ratio of the peak heights thereof.

In a preferred embodiment, the catalyst according to the present application may be prepared using a mixing method or an impregnation method, and more preferably using a slurry-mixing method.

In a further preferred embodiment, the catalyst can be prepared by a method comprising the steps of:

1) dissolving a vanadium-containing raw material and a chromium-containing raw material in an acid, and mixing the resultant with a solution of a M-containing raw material to obtain a first mixed solution;

2) mixing and reacting a phosphorus-containing raw material, water and a support to obtain a second mixed solution;

3) combining the first mixed solution with the second mixed solution and subjecting the resultant to concentration to obtain a mixed slurry; and 4) drying and calcining the mixed slurry to obtain the final catalyst.

In a still further preferred embodiment, the catalyst can be prepared by a method comprising the steps of:

1) dissolving an amount of the vanadium-containing raw material and the chromium-containing raw material in a heated acid solution, adding thereto the promoting element-containing raw material(s) other than the phosphorus-containing raw material, respectively, heating and stirring to obtain the first mixed solution;

2) adding the support into an aqueous phosphoric acid solution, and fully heating and stirring to obtain the second mixed solution;

3) slowly adding the first mixed solution to the second mixed solution, stirring and subjecting the resultant to concentration to obtain the mixed slurry with a certain solid content; and 4) drying and molding the mixed slurry to obtain a catalyst precursor, and calcining the catalyst precursor to obtain the final catalyst.

Particularly preferably, the catalyst precursor obtained in the step 4) is pre-calcined at a temperature of 300-350° C., and then calcined and activated at a temperature of 500-700° C. to obtain the final catalyst.

In a preferred embodiment, vanadium pentoxide, phosphoric acid and oxides of the elements corresponding to A, M in the formula are used as the starting materials for the active component of the catalyst according to the present application, or alternatively other compounds capable of being converted into the corresponding oxides by an appropriate method may also be used as the starting materials for the active component of the catalyst according to the present application.

Examples of useful starting materials include, but not limited to:

Vanadium-containing raw materials: vanadium pentoxide, ammonium metavanadate, vanadium sulfate and vanadium salts of organic acids such as vanadium oxalate and vanadium tartrate;

Chromium-containing raw materials: chromium sesquioxide and compounds that can be converted into chromium oxides by calcining;

A-containing raw materials: oxides, nitrates or other soluble compounds of A;

M-containing raw materials: oxides, nitrates or other soluble compounds of M;

Phosphorus-containing raw materials: phosphorus pentoxide, phosphomolybdic acid and phosphotungstic acid.

In a particularly preferred embodiment, the vanadium-containing raw material is selected from the group consisting of vanadium pentoxide, ammonium metavanadate, vanadium sulfate and vanadium salts of organic acids; the chromium-containing raw material is selected from the group consisting of chromium sesquioxide and compounds that can be converted into chromium oxides by calcining; the acid is selected from oxalic acid;

the M-containing raw material is selected from the group consisting of oxides, nitrates or other soluble compounds of M; and the phosphorus-containing raw material is selected from the group consisting of phosphorus pentoxide, phosphomolybdic acid and phosphotungstic acid.

In a second aspect, the present application provides A method for the preparation of a catalyst suitable for use as a fluidized-bed catalyst for the production of halogenated aromatic nitriles, the catalyst comprising an active component and a support, the active component being a complex having the following composition expressed in atomic ratio:

$$VP_aCr_bA_cM_dO_x$$

wherein:

A represents at least one metal selected from the group consisting of alkali metals and alkaline earth metals, preferably at least one selected from the group consisting of alkali metals;

M represents at least one element selected from the group consisting of Ti, Zr, Hf, La, Ce, Nb, Mo, W, Co, Zn, Fe, Ni, B, Sb, Bi, As, Ga, Ge, Sn and In;

a is in a range of 0-1.5;

b is in a range of 0.1-1;

c is in a range of 0-0.5;

d is in a range of 0-1;

x is the number of oxygen atoms required to satisfy the valence of each element in the active component;

the support being selected from the group consisting of silica and molecular sieves, the method comprising the steps of:

1) dissolving a vanadium-containing raw material and a chromium-containing raw material in an acid, and mixing the resultant with a solution of a M-containing raw material to obtain a first mixed solution;

2) mixing and reacting a phosphorus-containing raw material, water and a support to obtain a second mixed solution;

3) combining the first mixed solution with the second mixed solution and subjecting the resultant to concentration to obtain a mixed slurry; and 4) drying and calcining the mixed slurry to obtain the final catalyst.

In a preferred embodiment, the method comprises the steps of:

1) dissolving an amount of the vanadium-containing raw material and the chromium-containing raw material in a heated acid solution, adding thereto the promoting element-containing raw material(s) other than the phosphorus-containing raw material, respectively, heating and stirring to obtain the first mixed solution;

2) adding the support into an aqueous phosphoric acid solution, and fully heating and stirring to obtain the second mixed solution;

3) slowly adding the first mixed solution to the second mixed solution, stirring and subjecting the resultant to concentration to obtain the mixed slurry with a certain solid content; and 4) drying and molding the mixed slurry to obtain a catalyst precursor, and calcining the catalyst precursor to obtain the final catalyst.

In a further preferred embodiment, the catalyst precursor obtained in step 4) is pre-calcined at a temperature of 300-350° C., and then calcined and activated at a temperature of 500-700° C. to obtain the final catalyst.

In a preferred embodiment, in the XRD spectrum of the catalyst, diffraction peaks are present at 2θ=27.8±0.5° and 2θ=13.8±0.5°, and the ratio of the height ($I_1$) of the diffraction peak at 2θ=27.8±0.5° to the height ($I_2$) of the diffraction peak at 2θ=13.8±0.5°, i.e. $I_1$:$I_2$, is in a range from 3.5 to 6, preferably from 3.5 to 5.

In a preferred embodiment, in the composition of the composite, a is not 0; more preferably in a range from 0.5 to 1.5; even more preferably in a range from 0.5 to 1.0.

In a preferred embodiment, b is in a range from 0.1 to 0.7, more preferably in a range from 0.1 to 0.6.

In a preferred embodiment, c is in a range from 0.01 to 0.5, more preferably in a range from 0.01 to 0.3, and even more preferably in a range from 0.01 to 0.2.

In a preferred embodiment, d is in a range from 0.01 to 0.5.

In a further preferred embodiment, a is in a range from 0.5 to 1.5 and c is in a range from 0.01 to 0.5. More preferably, a is in a range from 0.5 to 1, b is in a range from 0.1 to 0.7, c is in a range from 0.01 to 0.3, and d is in a range from 0.01 to 0.5.

In a preferred embodiment, A is at least one of Na, K and Ca, more preferably at least one of K and Ca, and most preferably K.

In a preferred embodiment, M is at least one selected from the group consisting of Ti, Nb, Mo, W, Co, Zn, Fe, Ni, B, Sb, Bi and Sn, more preferably at least one selected from the group consisting of Mo, Nb, B and W.

In certain preferred embodiments, the active component of the catalyst may further comprise Se and/or Te in a molar ratio to V ranging from 0.01 to 0.2, preferably from 0.02 to 0.1.

In a preferred embodiment, the support is present in the catalyst in an amount ranging from 20% to 70% by weight, more preferably from 30% to 60% by weight.

In a preferred embodiment, a molecular sieve material is used as the support. In a further preferred embodiment, the support is a pure-silica molecular sieve. Particularly preferably, the pure-silica molecular sieve is one or more selected from the group consisting of MCM-41, MCM-48, SBA-1, SBA-2, SBA-15, SBA-16, MSU, Silicate-1, SSZ-13 and HMS, most preferably SSZ-13 molecular sieve.

In certain preferred embodiments, the support is a composite support composed of a pure-silica molecular sieve and silica, wherein the weight ratio of the pure-silica molecular sieve to silica is in a range from 1:9 to 9:1, more preferably from 1:4 to 4:1. Further preferably, the pure-silica molecular sieve in the composite support is one or more selected from the group consisting of MCM-41, MCM-48, SBA-1, SBA-2, SBA-15, SBA-16, MSU, Silicate-1, SSZ-13 and HMS. Particularly preferably, the support is a composite support of SSZ-13 molecular sieve and silica, and the weight ratio of the SSZ-13 molecular sieve to silica in the composite support is preferably in a range from 1:9 to 9:1, and more preferably from 1:4 to 4:1.

In a preferred embodiment, the vanadium-containing raw material is selected from the group consisting of vanadium pentoxide, ammonium metavanadate, vanadium sulfate and vanadium salts of organic acids; the chromium-containing raw material is selected from the group consisting of chromium sesquioxide and compounds that can be converted into chromium oxides by calcining; the acid is selected from oxalic acid; the M-containing raw material is selected from the group consisting of oxides, nitrates or other soluble compounds of M; and the phosphorus-containing raw material is selected from the group consisting of phosphorus pentoxide, phosphomolybdic acid and phosphotungstic acid.

In a third aspect, the present application provides a catalyst obtained by the method according to the present application.

In a fourth aspect, the present application provides the use of a catalyst according to the present application as a fluidized-bed catalyst for the production of halogenated aromatic nitriles.

In a fifth aspect, the present application provides a process for the production of halogenated aromatic nitriles, comprising the step of contacting and reacting a halogenated aromatic hydrocarbon with a catalyst according to the present application.

In a preferred embodiment, the halogenated aromatic nitrile is one or more selected from the group consisting of o-chlorobenzonitrile, m-chlorobenzonitrile, p-chlorobenzonitrile, o-bromobenzonitrile, m-bromobenzonitrile, p-bromobenzonitrile, dichlorobenzonitrile and dibromobenzonitrile, more preferably one or more selected from the group consisting of o-chlorobenzonitrile, m-chlorobenzonitrile, p-chlorobenzonitrile, p-bromobenzonitrile and dichlorobenzonitrile, and particularly preferably p-chlorobenzonitrile and dichlorobenzonitrile.

In a preferred embodiment, the contacting and reacting are carried out in the absence of bromoethane.

In some embodiments, the present application provides the following technical solutions:

Item 1: A fluidized-bed catalyst for the production of halogenated aromatic nitriles, comprising an active component and a support; the active component having the following composition expressed in atomic ratio:

$VP_aCr_bA_cM_dO_x$ wherein:

A is at least one element selected from the group consisting of alkali metals or alkaline earth metals;

M is at least one element selected from the group consisting of Ti, Zr, Hf, La, Ce, Nb, Cr, Mo, W, Co, Zn, Fe, Ni, B, Sb, Bi, As, Ga, Ge, Sn and In;

a is in a range of 0-1.5; b is in a range of 0.1-1; c is in a range of 0-0.5; d is in a range of 0-1; x is the number of oxygen atoms required to satisfy the valence of each element in the catalyst; and the support being silica or a molecular sieve.

Item 2: The fluidized-bed catalyst for the production of halogenated aromatic nitriles according to Item 1, characterized in that the ratio of the intensity of the main diffraction characteristic peak of $V_2O_5$ or $Cr_2O_3$ to the intensity of the main diffraction characteristic peak of $CrVO_4$ in the XRD spectrum of the catalyst is in a range from 0 to 0.5.

Item 3: The fluidized-bed catalyst for the production of halogenated aromatic nitriles according to Item 1, characterized in that, in the XRD spectrum of the catalyst, the ratio of the height ($I_1$) of the diffraction peak at $2\theta=27.8\pm0.5°$ to the height ($I_2$) of the diffraction peak at $2\theta=13.8\pm0.5°$, i.e. $I_1:I_2$, is in a range of 3.5-6.

Item 4: The fluidized-bed catalyst for the production of halogenated aromatic nitriles according to Item 1, characterized in that a is in a range of 0.5-1.5; and/or c is in a range of 0.01-0.5.

Item 5: The fluidized-bed catalyst for the production of halogenated aromatic nitriles according to Item 1, characterized in that A is at least one element selected from the group consisting of alkali metals.

Item 6: The fluidized-bed catalyst for the production of halogenated aromatic nitriles according to Item 1, characterized in that a is in a range of 0.5-1; and/or b is in a range of 0.1-0.7; and/or c is in a range of 0.01-0.3; and/or d is in a range of 0.01-0.5.

Item 7: The fluidized-bed catalyst for the production of halogenated aromatic nitriles according to Item 1, characterized in that the support is present in the catalyst in an amount ranging from 20% to 70% by weight.

Item 8: The fluidized-bed catalyst for the production of halogenated aromatic nitriles according to Item 1, characterized in that the support is a molecular sieve.

Item 9: The fluidized-bed catalyst for the production of halogenated aromatic nitriles according to Item 8, characterized in that the support is selected from the group consisting of pure-silica molecular sieves.

Item 10: The fluidized-bed catalyst for the production of halogenated aromatic nitriles according to Item 9, characterized in that the pure-silica molecular sieve is one or at least one selected from the group consisting of MCM-41, MCM-48, SBA-1, SBA-2, SBA-15, SBA-16, MSU, and HMS.

Item 11: A method for the production of halogenated aromatic nitriles, comprising the step of contacting and reacting a halogenated aromatic hydrocarbon with the catalyst according to any one of Items 1-10 to obtain a halogenated aromatic nitrile.

Item 12: The method for the production of halogenated aromatic nitriles according to Item 11, characterized in that the halogenated aromatic nitrile is one or at least one selected from the group consisting of (ortho, meta, para)-chlorobenzonitrile, (ortho, meta, para)-bromobenzonitrile, dichlorobenzonitrile, and dibromobenzonitrile.

The catalyst according to the present application can be used in a fluidized bed reactor with conventional design, and normally it is only required that the fluidization quality of the gas flow is ensured, the generation of abnormal fluidization phenomena such as "bubbles", "channel flow" and "slugging" during the fluidization process is reduced, and the degree of backmixing of the gas flow is reduced as much as possible, so that the selectivity of the reaction can be improved.

The catalyst according to the present application can be used in the production of a variety of halogenated aromatic nitriles including, but not limited to, o-chlorobenzonitrile, m-chlorobenzonitrile, p-chlorobenzonitrile, o-bromobenzonitrile, m-bromobenzonitrile, p-bromobenzonitrile, dichlorobenzonitrile and dibromobenzonitrile.

The catalyst according to the present application is usually used for the reaction under normal pressure, and can also be used for the reaction under pressurized condition, but the increase of the reaction pressure is not favorable for the improvement of the yield of the halogenated aromatic nitrile product. Therefore, it is preferable that the pressure of the reaction system should be kept at normal pressure or as close to normal pressure as possible.

The catalyst according to the present application has specific XRD spectrum peak(s), thereby showing a better ammoxidation activity, and is more suitable for industrial application. Particularly, when a pure-silica mesoporous molecular sieve is used as the support, the ammoxidation activity for halogenated aromatic hydrocarbons can be further remarkably improved. In addition, by using an active component having the specific composition in the catalyst according to the present application, a high selectivity of the catalyst can be maintained while reducing the chromium content without increasing the vanadium content, a balance between activity and selectivity can be kept, and the economical and environmental benefits of the catalyst can be effectively improved. In addition, when a composite support composed of a pure-silica molecular sieve and silica is used as the support of the catalyst, the selectivity of the target product can be unexpectedly and remarkably improved.

EXAMPLES

The present application is further illustrated by the following examples, which are not intended to limit the scope of the present application.

The conversion of halogenated aromatic hydrocarbons, the selectivity of aromatic nitriles and the yield of aromatic nitriles obtained in the examples using the catalyst according to the present application are defined as follows:

$$\text{Conversion of halogenated aromatic hydrocarbons } C\% = \frac{\text{Moles of halogenated aromatic hydrocarbons consumed in the reaction}}{\text{Moles of halogenated aromatic hydrocarbons fed to the reaction}} \times 100$$

$$\text{Selectivity of aromatic nitriles } S\% = \frac{\text{Moles of aromatic nitriles produced}}{\text{Moles of aromatic hydrocarbons consumed}} \times 100$$

$$\text{Single-pass yield of aromatic nitriles } Y\% = \frac{\text{Moles of aromatic nitriles produced}}{\text{Moles of aromatic hydrocarbons fed to the reaction}} \times 100$$

The evaluation of the performance of the catalyst according to the present application was carried out in a stainless steel fluidized bed reactor having a dimension of <p 38 mm×1800 mm, and the catalyst was added in an amount of 600 g.

Example 1

Preparation of the Catalyst:

0.5 mol of vanadium pentoxide (analytically pure, available from Sinopharm Chemical Reagent Co., Ltd) and 0.3 mol of chromium sesquioxide (analytically pure, available from Sinopharm Chemical Reagent Co., Ltd) were added into a 50 wt % oxalic acid solution containing 2 mol of oxalic acid (analytically pure, available from Sinopharm Chemical Reagent Co., Ltd) heated to 85° C., and fully stirred for reaction for 2 hours. While stirring was maintained, 0.02 mol of niobium pentoxide (2.5N, available from Sinopharm Chemical Reagent Co., Ltd) was added and the reaction was continued for 1 hour, and then 0.08 mol of potassium nitrate (analytically pure, available from Sinopharm Chemical Reagent Co., Ltd), phosphomolybdic acid (analytically pure, available from Sinopharm Chemical Reagent Co., Ltd) containing 0.1 mol of molybdenum, and deionized water were added to the solution and stirred uniformly to obtain a solution I.

About 215 g of SBA-15 pure-silica molecular sieve was added into 20 wt % phosphoric acid solution containing 0.8 mol of phosphoric acid (analytically pure, available from Sinopharm Chemical Reagent Co., Ltd), heated to 75° C. while stirring, and further continuously stirred for 2 h to obtain a second mixed solution II.

The solution I was slowly added into the solution II, heated while stirring to form a stable mixed solution, and then concentrated till a solid content of 45% (by weight) was obtained, thereby producing a viscous slurry.

Figure 1:
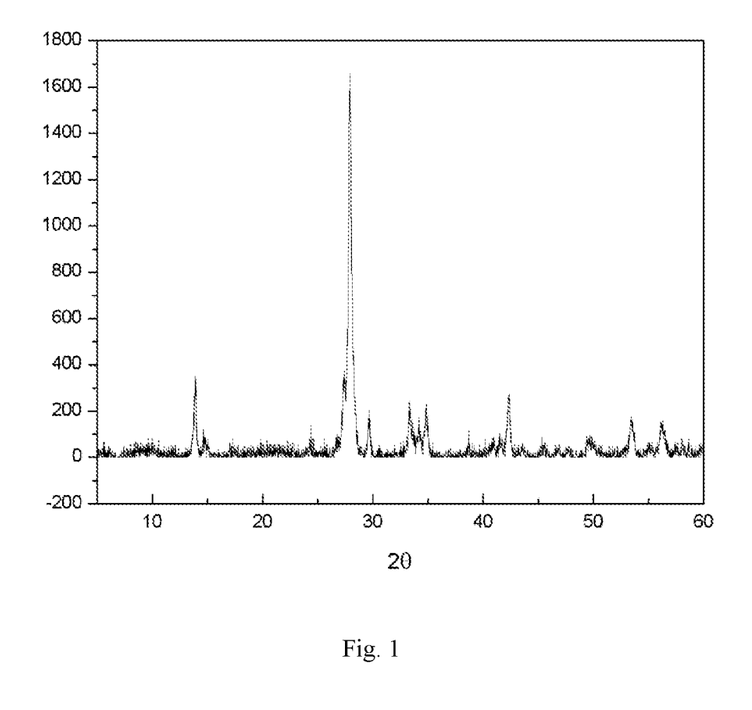
FIG. 1 is the XRD spectrum of the catalyst obtained in Example 1 of the present application.

The slurry was formed into a catalyst precursor by spray drying in a spray dryer, the resulting catalyst precursor was pre-calcined at 300° C. for 2 hours, and then calcined at 650° C. for 4.5 hours to obtain a catalyst with a composition expressed in atomic ratio (excluding O) of the active component being: $VP_{0.5}Cr_{0.6}K_{0.08}Mo_{0.1}Nb_{0.04}$, and the XRD spectrum of the catalyst is shown in FIG. 1. In the XRD test of the catalyst, the ratio of the height ($I_1$) of the diffraction peak at $2\theta=27.8°$ to the height ($I_2$) of the diffraction peak at $2\theta=13.8°$, i.e. $I_1:I_2$, is 4.56.

Evaluation of the Catalyst:

The catalyst obtained was used in the reaction for producing p-chlorobenzonitrile from p-chlorotoluene via ammoxidation, and the process conditions for the reaction were as follows:

a ratio of p-chlorotoluene:ammonia:air of 1:4:35 (mol);
a load of 0.06 $h^{-1}$ (WWH);
a reaction pressure of 0.1 MPa (gauge pressure); and
a reaction temperature of 420° C.;
and the results were as follows:
a conversion of p-chlorotoluene of 98.3%;
a selectivity of p-chlorobenzonitrile of 93.7%; and
a yield of p-chlorobenzonitrile of 92.1%.

Example 2

The preparation and evaluation of the catalyst were carried out in accordance with the method described in Example 1, except that a 20 wt % phosphoric acid solution containing 1.2 mol of phosphoric acid was used in place of the 20 wt % phosphoric acid solution containing 0.8 mol of phosphoric acid while the amount of the support was adjusted accordingly, so that the content of the support in the resulting catalyst was kept unchanged. The evaluation results are shown in Table 1.

Example 3

The preparation and evaluation of the catalyst were carried out in accordance with the method described in Example 1, except that the amount of chromium sesquioxide used was increased from 0.3 mol to 0.35 mol while the amount of the support was adjusted accordingly, so that the content of the support in the resulting catalyst was kept unchanged. The evaluation results are shown in Table 1.

Example 4

The preparation and evaluation of the catalyst were carried out in accordance with the method described in Example 1, except that the amount of potassium nitrate was increased from 0.08 mol to 0.25 mol while the amount of the support was adjusted accordingly, so that the content of the support in the resulting catalyst was kept unchanged. The evaluation results are shown in Table 1.

Example 5

The preparation and evaluation of the catalyst were carried out in accordance with the method described in Example 1, except that 0.06 mol of calcium nitrate (analytically pure, available from Sinopharm Chemical Reagent Co., Ltd) was used in place of the potassium nitrate, 0.5 mol of boric acid (analytically pure, available from Sinopharm Chemical Reagent Co., Ltd) was used in place of the phosphomolybdic acid, and 0.0067 mol of ammonium tungstate was used in place of the niobium pentoxide, while the amount of the support was adjusted accordingly, so that the content of the support in the resulting catalyst was kept unchanged. The evaluation results are shown in Table 1.

Example 6

The preparation and evaluation of the catalyst were carried out in accordance with the method described in Example 1, except that the amount of SBA-15 pure-silica molecular sieve was reduced from 215 g to 55 g. The evaluation results are shown in Table 1.

Example 7

The preparation and evaluation of the catalyst were carried out in accordance with the method described in Example 1, except that no phosphomolybdic acid or niobium pentoxide were added while the amount of the support was adjusted accordingly, so that the content of the support in the resulting catalyst was kept unchanged. The evaluation results are shown in Table 1.

Example 8

The preparation and evaluation of the catalyst were carried out in accordance with the method described in Example 1, except that 215 g of MCM-41 pure-silica molecular sieve was used in place of the SBA-15 pure-silica molecular sieve. The evaluation results are shown in Table 1.

Example 9

The preparation and evaluation of the catalyst were carried out in accordance with the method described in Example 1, except that 215 g of HMS pure-silica molecular sieve was used in place of the SBA-15 pure-silica molecular sieve. The evaluation results are shown in Table 1.

Example 10

The preparation and evaluation of the catalyst were carried out in accordance with the method described in Example 1, except that a mixture of 85 g of SBA-15 pure-silica molecular sieve and 130 g of HMS pure-silica molecular sieve was used in place of the SBA-15 pure-silica molecular sieve. The evaluation results are shown in Table 1.

Example 11

The preparation and evaluation of the catalyst were carried out in accordance with the method described in Example 1, except that a mixture of 194 g of MCM-48 pure-silica molecular sieve and 22 g of MSU pure-silica molecular sieve was used in place of the SBA-15 pure-silica molecular sieve. The evaluation results are shown in Table 1.

Example 12

The preparation and evaluation of the catalyst were carried out in accordance with the method described in Example 1, except that 215 g of Silicate-1 pure-silica molecular sieve was used in place of the SBA-15 pure-silica molecular sieve. The evaluation results are shown in Table 1.

Example 13

The preparation and evaluation of the catalyst were carried out in accordance with the method described in Example 1, except that 535 g of silica sol (reagent grade, Qingdao Haiyang Chemical Co., Ltd) containing 40% silica was used in place of the SBA-15 pure-silica molecular sieve. The evaluation results are shown in Table 1.

Example 14

The preparation and evaluation of the catalyst were carried out in accordance with the method described in Example 1, except that 0.1 mol of selenium dioxide (analytically pure, available from Sinopharm Chemical Reagent Co., Ltd) was used in place of phosphomolybdic acid and no niobium pentoxide was added, while the amount of the support was adjusted accordingly, so that the content of the support in the resulting catalyst was kept unchanged. The evaluation results are shown in Table 1.

Example 15

The preparation and evaluation of the catalyst were carried out in accordance with the method described in Example 14, except that 0.05 mol of telluric acid (analytically pure, available from Sinopharm Chemical Reagent Co., Ltd) was used in place of selenium dioxide, while the amount of the support was adjusted accordingly, so that the content of the support in the resulting catalyst was kept unchanged. The evaluation results are shown in Table 1.

Example 16

The preparation and evaluation of the catalyst were carried out in accordance with the method described in Example 14, except that a mixture of 0.02 mol of telluric acid and 0.03 mol of selenium dioxide was used in place of selenium dioxide, while the amount of the support was adjusted accordingly, so that the content of the support in the resulting catalyst was kept unchanged. The evaluation results are shown in Table 1.

Example 17

0.5 mol of vanadium pentoxide and 0.3 mol of chromium sesquioxide were added into 50 wt % oxalic acid solution containing 2 mol of oxalic acid heated to 85° C., and fully stirred for reaction for 2 h to obtain a solution I.

About 195 g of SBA-15 pure-silica molecular sieve was added into 20 wt % phosphoric acid solution containing 0.8 mol of phosphoric acid, heated to 75° C. while stirring, and further continuously stirred for 2 hours to obtain a solution II.

The solution I was slowly added into the solution II, heated while stirring to form a stable mixed solution, and concentrated till a solid content of 45% (by weight) was obtained, thereby producing a viscous slurry.

The slurry was formed into a catalyst precursor by spray drying in a spray dryer, the resulting catalyst precursor was pre-calcined at 300° C. for 2 hours, and then calcined at 650° C. for 4.5 hours to obtain a catalyst with a composition expressed in atomic ratio (excluding O) of the active component being: $VP_{0.8}Cr_{0.6}$. In the XRD test of the catalyst, the ratio of the height ($I_1$) of the diffraction peak at $2\theta=27.8°$ to the height ($I_2$) of the diffraction peak at $2\theta=13.8°$, i.e. $I_1:I_2$, is 3.90.

The catalyst obtained was used in the reaction for producing p-chlorobenzonitrile from p-chlorotoluene via ammoxidation under the same reaction conditions as in Example 1, and the evaluation results are shown in Table 1.

Example 18

0.5 mol of vanadium pentoxide and 0.3 mol of chromium sesquioxide were added into 50 wt % oxalic acid solution containing 2 mol of oxalic acid heated to 85° C., and fully stirred for reaction for 2 h to obtain a solution I.

About 195 g of SSZ-13 pure-silica molecular sieve was added into 20 wt % phosphoric acid solution containing 0.8 mol of phosphoric acid, heated to 75° C. while stirring, and further continuously stirred for 2 h to obtain a solution II.

The solution I was slowly added into the solution II, heated while stirring to form a stable mixed solution, and concentrated till a solid content of 45% (by weight) was obtained, thereby producing a viscous slurry.

The slurry was formed into a catalyst precursor by spray drying in a spray dryer, the resulting catalyst precursor was pre-calcined at 300° C. for 2 hours, and then calcined at 650° C. for 4.5 hours to obtain a catalyst with a composition expressed in atomic ratio (excluding O) of the active component being: $VP_{0.8}Cr_{0.6}$. In the XRD test of the catalyst, the ratio of the height ($I_1$) of the diffraction peak at $2\theta=27.8°$ to the height ($I_2$) of the diffraction peak at $2\theta=13.8°$, i.e. $I_1:I_2$, is 4.16.

The catalyst obtained was used in the reaction for producing p-chlorobenzonitrile from p-chlorotoluene via ammoxidation under the same reaction conditions as in Example 1, and the evaluation results are shown in Table 1.

Example 19

0.5 mol of vanadium pentoxide and 0.3 mol of chromium sesquioxide were added into 50 wt % oxalic acid solution containing 2 mol of oxalic acid heated to 85° C., and fully stirred for reaction for 2 h to obtain a solution I.

50 g of SSZ-13 pure-silica molecular sieve and 145 g of silica were added into 20 wt % phosphoric acid solution containing 0.8 mol of phosphoric acid, heated to 75° C. while stirring, and further continuously stirred for 2 h to obtain a solution II.

The solution I was slowly added into the solution II, heated while stirring to form a stable mixed solution, and concentrated till a solid content of 45% (by weight) was obtained, thereby producing a viscous slurry.

The slurry was formed into a catalyst precursor by spray drying in a spray dryer, the resulting catalyst precursor was pre-calcined at 300° C. for 2 hours, and then calcined at 650° C. for 4.5 hours to obtain a catalyst with a composition expressed in atomic ratio (excluding O) of the active component being: $VP_{0.8}Cr_{0.6}$. In the XRD test of the catalyst, the ratio of the height ($I_1$) of the diffraction peak at $2\theta=27.8°$ to the height ($I_2$) of the diffraction peak at $2\theta=13.8°$, i.e. $I_1:I_2$, is 4.30.

The catalyst obtained was used in the reaction for producing p-chlorobenzonitrile from p-chlorotoluene via ammoxidation under the same reaction conditions as in Example 1, and the evaluation results are shown in Table 1.

Example 20

0.5 mol of vanadium pentoxide and 0.3 mol of chromium sesquioxide were added into 50 wt % oxalic acid solution containing 2 mol of oxalic acid heated to 85° C., and fully stirred for reaction for 2 h to obtain a solution I.

145 g of SSZ-13 molecular sieve and 50 g of silica were added into 20 wt % phosphoric acid solution containing 0.8 mol of phosphoric acid, heated to 75° C. while stirring, and further continuously stirred for 2 hours to obtain a solution II.

The solution I was slowly added into the solution II, heated while stirring to form a stable mixed solution, and concentrated till a solid content of 45% (by weight) was obtained, thereby producing a viscous slurry.

The slurry was formed into a catalyst precursor by spray drying in a spray dryer, the resulting catalyst precursor was pre-calcined at 300° C. for 2 hours, and then calcined at 650° C. for 4.5 hours to obtain a catalyst with a composition expressed in atomic ratio (excluding O) of the active component being: $VP_{0.8}Cr_{0.6}$. In the XRD test of the catalyst, the ratio of the height ($I_1$) of the diffraction peak at 2θ=27.8° to the height ($I_2$) of the diffraction peak at 2θ=13.8°, i.e. $I_1:I_2$, is 4.27.

The catalyst obtained was used in the reaction for producing p-chlorobenzonitrile from p-chlorotoluene via ammoxidation under the same reaction conditions as in Example 1, and the evaluation results are shown in Table 1.

Example 21

0.5 mol of vanadium pentoxide and 0.3 mol of chromium sesquioxide were added into 50 wt % oxalic acid solution containing 2 mol of oxalic acid heated to 85° C., and fully stirred for reaction for 2 h. While stirring, 0.02 mol of niobium pentoxide was added and further reacted for 1 h, 0.08 mol of potassium nitrate, phosphomolybdic acid containing 0.1 mol of molybdenum and deionized water were then added into the solution, and stirred uniformly to obtain a solution I.

About 54 g of SSZ-13 molecular sieve and 162 g of silica were added into a 20 wt % phosphoric acid solution containing 0.8 mol of phosphoric acid, heated to 75° C. while stirring, and further continuously stirred for 2 hours to obtain a solution II.

The solution I was slowly added into the solution II, heated while stirring to form a stable mixed solution, and concentrated till a solid content of 45% (by weight) was obtained, thereby producing a viscous slurry.

The slurry was formed into a catalyst precursor by spray drying in a spray dryer, the resulting catalyst precursor was pre-calcined at 300° C. for 2 hours, and then calcined at 650° C. for 4.5 hours to obtain a catalyst with a composition expressed in atomic ratio (excluding O) of the active component being: $VP_{0.8}Cr_{0.6}K_{0.08}Mo_{0.1}Nb_{0.04}$. In the XRD test of the catalyst, the ratio of the height ($I_1$) of the diffraction peak at 2θ=27.8° to the height ($I_2$) of the diffraction peak at 2θ=13.8°, i.e. $I_1:I_2$, is 4.67.

The catalyst obtained was used in the reaction for producing p-chlorobenzonitrile from p-chlorotoluene via ammoxidation under the same reaction conditions as in Example 1, and the evaluation results are shown in Table 1.

Comparative Example 1

0.5 mol of vanadium pentoxide was added into 50 wt % oxalic acid solution containing 2 mol of oxalic acid, fully stirred, and reacted for 2 h to obtain a vanadium-containing solution. 85 wt % phosphoric acid containing 0.8 mol of phosphoric acid, 0.08 mol of potassium nitrate, molybdophosphoric acid containing 0.1 mol of molybdenum, 0.6 mol of chromium nitrate (analytically pure, available from Sinopharm Chemical Reagent Co., Ltd), 0.04 mol of niobium oxalate (analytically pure, available from Sinopharm Chemical Reagent Co., Ltd) and deionized water were sequentially added while stirring, and 215 g of SBA-15 pure-silica molecular sieve was slowly added to the above solution while stirring, further stirred to obtain a stable mixed solution, and then evaporated by heating till a solid content of 45 wt % was obtained, thereby producing a viscous slurry.

Figure 2:
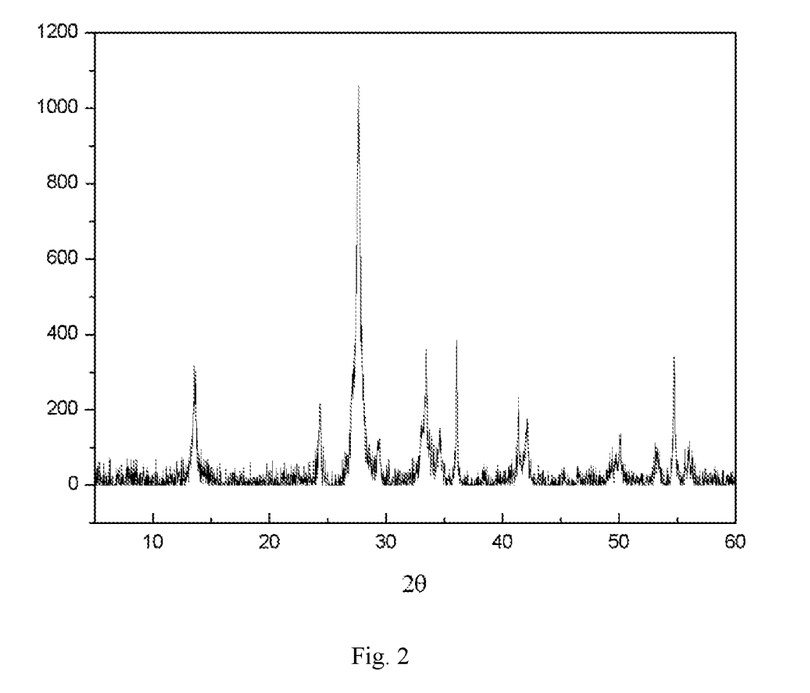
FIG. 2 is the XRD spectrum of the catalyst obtained in Comparative Example 1.

The slurry was formed into a catalyst precursor by spray drying in a spray dryer, the resulting catalyst precursor was pre-calcined at 300° C. for 2 hours, and then calcined at 650° C. for 4.5 hours to obtain a catalyst with a composition expressed in atomic ratio (excluding O) of the active component being: $VP_{0.8}Cr_{0.6}K_{0.08}Mo_{0.1}Nb_{0.04}$. The XRD spectrum of the catalyst is shown in FIG. 2. In the XRD test of the catalyst, the ratio of the height ($I_1$) of the diffraction peak at 2θ=27.8° to the height ($I_2$) of the diffraction peak at 2θ=13.8°, i.e. $I_1:I_2$, is 3.34.

The catalyst obtained was used in the ammoxidation reaction of p-chlorotoluene under the same evaluation conditions as in Example 1, and the evaluation results are shown in Table 1.

Comparative Example 2

0.5 mol of vanadium pentoxide was added into 50 wt % oxalic acid solution containing 2 mol of oxalic acid, fully stirred, and reacted for 2 h to obtain a vanadium-containing solution. 85 wt % phosphoric acid containing 1.5 mol of phosphoric acid, 0.08 mol of potassium nitrate, phosphomolybdic acid containing 0.1 mol of molybdenum, 0.04 mol of niobium oxalate and deionized water were sequentially added while stirring, and an alumina sol (reagent grade, available from Sinopharm Chemical Reagent Co., Ltd) containing 200 g of alumina was slowly added to the above solution while stirring, further stirred to obtain a stable mixed solution, and then evaporated by heating till a solid content of 45 wt % was obtained, thereby producing a viscous slurry. The slurry was formed into a catalyst precursor by spray drying in a spray dryer, the resulting catalyst precursor was pre-calcined at 300° C. for 2 hours, and then calcined at 650° C. for 4.5 hours to obtain a catalyst with a composition expressed in atomic ratio (excluding O) of the active component being: $VP_{1.5}K_{0.08}Mo_{0.1}Nb_{0.04}$.

The catalyst obtained was used in the ammoxidation reaction of p-chlorotoluene under the same evaluation conditions as in Example 1, and the evaluation results are shown in Table 1.

Comparative Example 3

0.5 mol of vanadium pentoxide and 0.3 mol of chromium sesquioxide were added into 50 wt % oxalic acid solution containing 5 mol of oxalic acid, fully heated to 60° C., stirred and reacted for 2 h to obtain a vanadium-chromium solution. 85 wt % phosphoric acid containing 0.8 mol of phosphoric acid, 0.08 mol of potassium nitrate, phosphomolybdic acid containing 0.1 mol of molybdenum, 0.04 mol of niobium oxalate and deionized water were sequentially added while stirring, stirred for 1 hour, silica sol containing about 215 g of silica was then slowly added to the above solution while stirring, further stirred to form a stable mixed solution, then evaporated by heating till a solid content of 45 wt % was obtained, thereby producing a viscous slurry. The slurry was formed into a catalyst precursor by spray drying in a spray dryer, the resulting catalyst precursor was calcined at 650° C. for 5 hours to obtain a catalyst with a composition expressed in atomic ratio (excluding 0) of the active component being: $VP_{0.8}Cr_{0.6}K_{0.08}Mo_{0.1}Nb_{0.04}$.

The catalyst obtained was used in the ammoxidation reaction of p-chlorotoluene under the same evaluation conditions as in Example 1, and the evaluation results are shown in Table 1.

Comparative Example 4

0.5 mol of vanadium pentoxide and 0.3 mol of chromium sesquioxide were added into 50 wt % oxalic acid solution containing 5 mol of oxalic acid, fully heated to 60° C., stirred and reacted for 2 h to obtain a vanadium-chromium solution. 85 wt % phosphoric acid containing 0.8 mol of phosphoric acid and deionized water were sequentially added while stirring, stirred and reacted for 1 hour, a solution containing about 50 g of SSZ-13 pure-silica molecular sieve and 145 g of silica was then slowly added to the above solution while stirring, further stirred to obtain a stable mixed solution, then evaporated by heating till a solid content of 45 wt % was obtained, thereby producing a viscous slurry. The slurry was formed into a catalyst precursor by spray drying in a spray dryer, the resulting catalyst precursor was pre-calcined at 300° C. for 2 hours, and then calcined at 650° C. for 4.5 hours to obtain a catalyst with a composition expressed in atomic ratio (excluding O) of the active component being: $VP_{0.8}Cr_{0.6}$.

The catalyst obtained was used in the ammoxidation reaction of p-chlorotoluene under the same evaluation conditions as in Example 1, and the evaluation results are shown in Table 1.

as the support is beneficial to further improve the ammoxidation activity of the catalyst for halogenated aromatic hydrocarbons (see, for example, Examples 1 and 8-12, etc.), and the use of a composite support of a pure-silica molecular sieve and silica can further improve the selectivity of the target product (see, for example, Examples 19-21, etc.).

Example 22

The catalyst prepared by the method of Example 1 was used in the ammoxidation of o-chlorotoluene under the following reaction conditions:
 a ratio of o-chlorotoluene:ammonia:air of 1:3.5:20 (mol);
 a load of 0.06 $h^{-1}$ (WWH);
 a reaction pressure of 0.1 MPa (gauge pressure);
 a reaction temperature of 415° C.

The evaluation results show that the conversion of o-chlorotoluene is 98.5%, and the selectivity of o-chlorobenzonitrile is 92.6%.

Example 23

The catalyst prepared by the method of Example 1 was used in the ammoxidation of m-chlorotoluene under the following reaction conditions:

TABLE 1

Properties and performances of the catalysts obtained in the Examples and Comparative Examples

| Ex. | Composition of the active component (excluding O) | Support | Content of Support wt. % | Ratio of diffraction peaks, $I_1:I_2$ | Conversion of P-chlorotoluene, % | Selectivity of P-chlorobenzonitrile, mol % |
|---|---|---|---|---|---|---|
| 1 | $VP_{0.8}Cr_{0.6}K_{0.08}Mo_{0.1}Nb_{0.04}$ | SBA-15 | 50 | 4.56 | 98.3 | 93.7 |
| 2 | $VP_{1.2}Cr_{0.6}K_{0.08}Mo_{0.1}Nb_{0.04}$ | SBA-15 | 50 | 4.37 | 97.6 | 88.7 |
| 3 | $VP_{0.8}Cr_{0.7}K_{0.08}Mo_{0.1}Nb_{0.04}$ | SBA-15 | 50 | 4.50 | 97.2 | 92.7 |
| 4 | $VP_{0.8}Cr_{0.6}K_{0.25}Mo_{0.1}Nb_{0.04}$ | SBA-15 | 50 | 4.09 | 98.6 | 89.6 |
| 5 | $VP_{0.8}Cr_{0.6}Ca_{0.06}B_{0.5}W_{0.08}$ | SBA-15 | 50 | 3.88 | 99.1 | 88.8 |
| 6 | $VP_{0.8}Cr_{0.6}K_{0.08}M_{0.01}Nb_{0.04}$ | SBA-15 | 20 | 4.40 | 95.8 | 89.6 |
| 7 | $VP_{0.8}Cr_{0.6}K_{0.08}$ | SBA-15 | 50 | 4.21 | 97.9 | 90.0 |
| 8 | $VP_{0.8}Cr_{0.6}K_{0.08}Mo_{0.1}Nb_{0.04}$ | MCM-41 | 50 | 4.65 | 98.6 | 92.6 |
| 9 | $VP_{0.8}Cr_{0.6}K_{0.08}Mo_{0.1}Nb_{0.04}$ | HMS | 50 | 4.47 | 98.6 | 91.5 |
| 10 | $VP_{0.8}Cr_{0.6}K_{0.08}Mo_{0.1}Nb_{0.04}$ | SBA-15(40%)/HMS(60%) | 50 | 4.55 | 98.5 | 93.2 |
| 11 | $VP_{0.8}Cr_{0.6}K_{0.08}Mo_{0.1}Nb_{0.04}$ | MCM-48/(90%)/MSU(10%) | 50 | 4.37 | 99.0 | 90.9 |
| 12 | $VP_{0.8}Cr_{0.6}K_{0.08}Mo_{0.1}Nb_{0.04}$ | Silicate-1 | 50 | 4.46 | 98.2 | 86.3 |
| 13 | $VP_{0.8}Cr_{0.6}K_{0.08}Mo_{0.1}Nb_{0.04}$ | $SiO_2$ | 50 | 4.39 | 95.6 | 89.1 |
| 14 | $VP_{0.8}Cr_{0.6}K_{0.08}Se_{0.1}$ | SBA-15 | 50 | 4.24 | 98.1 | 92.3 |
| 15 | $VP_{0.8}Cr_{0.6}K_{0.08}Te_{0.05}$ | SBA-15 | 50 | 4.25 | 98.4 | 92.2 |
| 16 | $VP_{0.8}Cr_{0.6}K_{0.08}Se_{0.03}Te_{0.02}$ | SBA-15 | 50 | 4.42 | 99.0 | 93.2 |
| 17 | $VP_{0.8}Cr_{0.6}$ | SBA-15 | 50 | 3.90 | 95.5 | 86.2 |
| 18 | $VP_{0.8}Cr_{0.6}$ | SSZ-13 | 50 | 4.16 | 97.5 | 90.2 |
| 19 | $VP_{0.8}Cr_{0.6}$ | SSZ-13(25%)/$SiO_2$(75%) | 50 | 4.30 | 98.6 | 93.2 |
| 20 | $VP_{0.8}Cr_{0.6}$ | SSZ-13(75%)/$SiO_2$(25%) | 50 | 4.27 | 99.0 | 93.0 |
| 21 | $VP_{0.8}Cr_{0.6}K_{0.08}Mo_{0.1}Nb_{0.04}$ | SSZ-13(25%)/$SiO_2$(75%) | 50 | 4.67 | 98.9 | 93.9 |
| Comp. Ex. 1 | $VP_{0.8}Cr_{0.6}K_{0.08}Mo_{0.1}Nb_{0.04}$ | SBA-15 | 50 | 3.34 | 98.2 | 76.5 |
| Comp. Ex. 2 | $VP_{1.5}K_{0.08}Mo_{0.1}Nb_{0.04}$ | $Al_2O_3$ | 50 | NA | 92.9 | 67.3 |
| Comp. Ex. 3 | $VP_{0.8}Cr_{0.6}K_{0.08}Mo_{0.1}Nb_{0.04}$ | $SiO_2$ | 50 | 2.78 | 95.0 | 82.1 |
| Comp. Ex. 4 | $VP_{0.8}Cr_{0.6}$ | SSZ-13(25%)/$SiO_2$(75%) | 50 | 3.15 | 98.0 | 83.5 |

As can be seen from the results of Table 1, the catalysts according to the present application obtained in Examples 1-21 show significantly improved catalytic performances, particularly significantly improved product selectivity, as compared to the catalysts obtained in Comparative Examples 1-4. In addition, for the catalyst according to the present application, the use of pure-silica molecular sieves a ratio of m-chlorotoluene:ammonia:air of 1:4:20 (mol);
 a load of 0.06 $h^{-1}$ (WWH);
 a reaction pressure of 0.1 MPa (gauge pressure);
 a reaction temperature of 420° C.

The evaluation results show that the conversion of m-chlorotoluene is 98.8%, and the selectivity of m-chlorobenzonitrile is 91.0%.

Example 24

The catalyst prepared by the method of Example 1 was used in the ammoxidation of p-bromotoluene under the following reaction conditions:
  a ratio of p-bromotoluene:ammonia:air of 1:4:20 (mol);
  a load of 0.06 h$^{-1}$ (WWH);
  a reaction pressure of 0.1 MPa (gauge pressure);
  a reaction temperature of 405° C.

The evaluation results show that the conversion of p-bromotoluene is 98.9% and the selectivity of p-bromobenzonitrile is 89.1%.

Example 25

The catalyst prepared by the method of Example 1 was used in the ammoxidation of 2,6-dichlorotoluene under the following reaction conditions:
  a ratio of 2,6-dichlorotoluene:ammonia:air of 1:4:20 (mol);
  a load of 0.06 h$^{-1}$ (WWH);
  a reaction pressure of 0.1 MPa (gauge pressure);
  a reaction temperature of 415° C.

The evaluation results show that the conversion of 2,6-dichlorotoluene is 98.0%, and the selectivity of 2,6-dichlorobenzonitrile is 87.9%.

Example 26

The catalyst prepared by the method of Example 1 was used in the ammoxidation of 3,4-dichlorotoluene under the following reaction conditions:
  a ratio of 3,4-dichlorotoluene:ammonia:air of 1:4:20 (mol);
  a load of 0.06 h$^{-1}$ (WWH);
  a reaction pressure of 0.1 MPa (gauge pressure);
  a reaction temperature of 415° C.

The evaluation results show that the conversion of 3,4-dichlorotoluene is 98.4%, and the selectivity of 3,4-dichlorobenzonitrile is 88.6%.

Example 27

The catalyst prepared by the method of Example 13 was used in the ammoxidation of 2,6-dichlorotoluene under the following reaction conditions:
  a ratio of 2,6-dichlorotoluene:ammonia:air of 1:4:20 (mol);
  a load of 0.06 h$^{-1}$ (WWH);
  a reaction pressure of 0.1 MPa (gauge pressure);
  a reaction temperature of 415° C.

The evaluation results show that the conversion of 2,6-dichlorotoluene is 96.8%, and the selectivity of 2,6-dichlorobenzonitrile is 87.7%.

Comparative Example 5

A catalyst was prepared as described in Example 1 of Chinese patent application publication CN 1230465A. 165.7 g of vanadium pentoxide was added to a solution composed of 360 ml of water and 345 g of oxalic acid, and fully stirred to obtain a vanadium oxalate solution. 182.2 g of chromic oxide (analytically pure, available from Sinopharm Chemical Reagent Co., Ltd) was slowly added to a solution of 695.5 g oxalic acid and 450 ml water at 50-60° C., and stirred to obtain a chromium oxalate solution. The vanadium oxalate solution and the chromium oxalate solution were mixed at 50-60° C. to obtain a vanadium-chromium solution. 160.6 g of ammonium molybdate (analytically pure, available from Sinopharm Chemical Reagent Co., Ltd) and 105 g of 85% phosphoric acid were added into 1L of water and mixed to obtain a molybdenum-phosphorus solution.

The vanadium-chromium solution and the molybdenum-phosphorus solution were fully mixed, 1250 g of silica sol containing 40% of silica was added thereto, heated while stirring, and evaporated till a solid content of 38% was obtained, to produce a slurry. The slurry was spray formed to obtain the catalyst. The composition of the active component of the resulting catalyst expressed in atomic ratio (excluding O) is: $V_1Cr_1P_{0.5}Mo_{0.5}$. In the XRD test of the catalyst, the ratio of the height ($I_1$) of the diffraction peak at 2θ=27.8° to the height ($I_2$) of the diffraction peak at 2θ=13.8°, i.e. $I_1:I_2$, is 3.05.

The catalyst was used in the ammoxidation reaction of p-chlorotoluene, and evaluated under the same reaction conditions as in Example 1, and the evaluation results show that the conversion of p-chlorotoluene is 90.1% and the selectivity of p-chlorobenzonitrile is 82.5%.

Comparative Example 6

The catalyst obtained in Comparative Example 5 was used in the ammoxidation of o-chlorotoluene under the same reaction conditions as in Example 22, and the evaluation results show that the conversion of o-chlorotoluene is 87.9% and the selectivity of o-chlorobenzonitrile is 80.2%.

Comparative Example 7

The catalyst obtained in Comparative Example 5 was used in the ammoxidation of 2,6-dichlorotoluene under the same reaction conditions as in Example 25, and the evaluation results show that the conversion of 2,6-dichlorotoluene is 88.6% and the selectivity of 2,6-dichlorobenzonitrile is 78.5%.

Comparative Example 8

The catalyst was prepared as described in Example 1 of Chinese patent application publication CN 1187320C. 224 g of vanadium pentoxide was added into a solution composed of 490 ml of water and 468 g of oxalic acid at a temperature of 80-90° C., fully stirred and reacted to obtain a vanadium oxalate solution. 1250 g of silica sol containing 40 wt % of silica was slowly added into the above solution under stirring. Then, a solution composed of 864 g of chromium nitrate, 12.4 g of potassium nitrate, 71.6 g of cobalt nitrate (analytically pure, available from Sinopharm Chemical Reagent Co., Ltd) and 500 ml of water, a solution composed of 76.4 g of boric acid (analytically pure, available from Sinopharm Chemical Reagent Co., Ltd), 85.1 g of 85% phosphoric acid and 500 ml of water, and a solution composed of 43.5 g of ammonium molybdate and 100 ml of water were respectively added, stirred and evaporated by heating till a solid content of 40% was obtained, thereby producing a viscous slurry. The slurry was formed into a catalyst precursor by spray drying in a spray dryer, the resulting catalyst precursor was pre-calcined at 300° C. for 2 hours, and then calcined at 650° C. for 4.5 hours to obtain the active catalyst. The composition of the active component of the resulting catalyst expressed in atomic ratio (excluding O) is: $V_1Cr_{0.9}B_{0.8}P_{0.3}Mo_{0.1}Co_{0.1}K_{0.05}$. In the XRD test of the catalyst, the ratio of the height ($I_1$) of the diffraction peak at 2θ=27.80 to the height ($I_2$) of the diffraction peak at 2θ=13.8°, i.e. $I_1$:$I_2$, is 3.12.

The catalyst was used in the ammoxidation of 2,6-dichlorotoluene under the same reaction conditions as in Example 25, and the evaluation results show that the conversion of 2,6-dichlorotoluene is 92.6% and the selectivity of 2,6-dichlorobenzonitrile is 80.5%.

Comparative Example 9

A catalyst was prepared as described in Example 1 of Chinese patent application publication CN 1223579C. 224 g of vanadium pentoxide was added into a solution composed of 490 ml of water and 468 g of oxalic acid at a temperature of 80-90° C., fully stirred and reacted to obtain a vanadium oxalate solution. 1250 g of silica sol containing 40 wt % of silica was slowly added into the above solution under stirring. Then, a solution composed of 864 g of chromium nitrate, 12.4 g of potassium nitrate and 500 ml of water, a solution composed of 76.4 g of boric acid, 85.1 g of 85% phosphoric acid and 500 ml of water, and a solution composed of 43.5 g of ammonium molybdate and 100 ml of water were respectively added, stirred and evaporated by heating till a solid content of 40% was obtained, thereby producing a viscous slurry. The slurry was formed into a catalyst precursor by spray drying in a spray dryer, the resulting catalyst precursor was pre-calcined at 300° C. for 2 hours, and then calcined at 650° C. for 4.5 hours to obtain the active catalyst. The composition of the active component of the resulting catalyst expressed in atomic ratio (excluding O) is: $V_1Cr_{0.9}B_{0.8}P_{0.3}Mo_{0.1}K_{0.05}$. In the XRD test of the catalyst, the ratio of the height ($I_1$) of the diffraction peak at 2θ=27.8° to the height ($I_2$) of the diffraction peak at 2θ=13.8°, i.e. $I_1$:$I_2$, is 3.03.

The catalyst was used in the ammoxidation of 2,6-dichlorotoluene under the same reaction conditions as in Example 25, and the evaluation results show that the conversion of 2,6-dichlorotoluene is 90.7% and the selectivity of 2,6-dichlorobenzonitrile is 80.7%.

Comparative Example 10

The catalyst was prepared as described in Example 1 of Chinese patent application publication CN 1252043C. 224 g of vanadium pentoxide was added into a solution composed of 490 ml of water and 468 g of oxalic acid at a temperature of 80-90° C., fully stirred and reacted to obtain a vanadium oxalate solution. 1250 g of silica sol containing 40 wt % of silica was slowly added to the above solution under stirring. Then, a solution composed of 886 g of chromium nitrate and 300 ml of water, a solution composed of 76.3 g of boric acid and 560 ml of water, and a solution composed of 85 g of 85% phosphoric acid and 50 ml of water were respectively added, and 20 ml of an aqueous solution containing 24.9 g of potassium nitrate was finally added, stirred, and evaporated by heating till a solid content of 40% was obtained, thereby producing a viscous slurry. The slurry was formed into a catalyst precursor by spray drying in a spray dryer, the resulting catalyst precursor was calcined at 650° C. for 5 hours to obtain the active catalyst. The composition of the active component of the resulting catalyst expressed in atomic ratio (excluding O) is: $V_1Cr_{0.9}B_{0.5}P_{0.3}K_{0.1}$. In the XRD test of the catalyst, the ratio of the height ($I_1$) of the diffraction peak at 2θ=27.8° to the height (12) of the diffraction peak at 2θ=13.8°, i.e. $I_1$:$I_2$, is 2.72.

The catalyst was used in the ammoxidation of 2,6-dichlorotoluene under the same reaction conditions as in Example 25, and the evaluation results show that the conversion of 2,6-dichlorotoluene is 93.5% and the selectivity of 2,6-dichlorobenzonitrile is 74.2%.

Comparative Example 11

201 g of vanadium pentoxide was added into a solution composed of 3000 ml of water and 420 g of oxalic acid at a temperature of 80-90° C., fully stirred, and reacted to obtain a vanadium oxalate solution. 1250 g of silica sol containing 40 wt % of silica was slowly added to the above solution under stirring. Then, a solution composed of 798 g of chromium nitrate and 900 ml of water, a solution composed of 68.6 g of boric acid and 560 ml of water, a solution composed of 273 g of ammonium molybdate and 200 ml of water, and 0.11 mol of phosphoric acid solution were respectively added, a solution composed of 11 g of potassium nitrate and 30 ml of water were finally added, mixed under stirring, and evaporated by heating till a solid content of 35 wt % was obtained, thereby producing a viscous slurry. The slurry was spray formed into a catalyst, the resulting catalyst was dried at 120° C. for 12 h, and calcined at 550° C. for 8 h to obtain the active catalyst. The composition of the active component of the resulting catalyst expressed in atomic ratio (excluding O) is: $V_1Cr_{0.9}B_{0.8}P_{0.05}Mo_{0.45}K_{0.05}$. In the XRD test of the catalyst, the ratio of the height ($I_1$) of the diffraction peak at 2θ=27.8° to the height ($I_2$) of the diffraction peak at 2θ=13.8°, i.e. $I_1$:$I_2$, is 2.89.

The catalyst was used in the ammoxidation of 2,6-dichlorotoluene under the same reaction conditions as in Example 25, and the evaluation results show that the conversion of 2,6-dichlorotoluene is 88.6% and the selectivity of 2,6-dichlorobenzonitrile is 81.2%.

TABLE 2

Properties and performances of the catalysts obtained in the Examples and Comparative Examples

| Ex. | Composition of the active component (excluding O) | Ratio of diffraction peaks, $I_1$:$I_2$ | Raw material of the reaction | Conversion of the raw material, % | Selectivity of aromatic nitriles, mol % |
|---|---|---|---|---|---|
| 1 | $VP_{0.8}Cr_{0.6}K_{0.08}Mo_{0.1}Nb_{0.04}$ | 4.56 | p-chlorotoluene | 98.3 | 93.7 |
| 22 | | | o-chlorotoluene | 98.5 | 92.6 |
| 23 | | | m-chlorotoluene | 98.8 | 91.0 |
| 24 | | | p-bromotoluene | 98.9 | 89.1 |
| 25 | | | 2,6-dichlorotoluene | 98.0 | 87.9 |
| 26 | | | 3,4-dichlorotoluene | 98.4 | 88.6 |
| 27 | $VP_{0.8}Cr_{0.6}K_{0.08}Mo_{0.1}Nb_{0.04}$ | 4.39 | 2,6-dichlorotoluene | 96.8 | 87.7 |

TABLE 2-continued

Properties and performances of the catalysts obtained in the Examples and Comparative Examples

| Ex. | Composition of the active component (excluding O) | Ratio of diffraction peaks, $I_1:I_2$ | Raw material of the reaction | Conversion of the raw material, % | Selectivity of aromatic nitriles, mol % |
|---|---|---|---|---|---|
| Comp. Ex. 5 | $V_1Cr_1P_{0.5}Mo_{0.5}$ | 3.05 | p-chlorotoluene | 90.1 | 82.5 |
| Comp. Ex. 6 | | | o-chlorotoluene | 87.9 | 80.2 |
| Comp. Ex. 7 | | | 2,6-dichlorotoluene | 88.6 | 78.5 |
| Comp. Ex. 8 | $V_1Cr_{0.9}B_{0.5}P_{0.3}Mo_{0.1}Co_{0.1}K_{0.05}$ | 3.12 | 2,6-dichlorotoluene | 92.6 | 80.5 |
| Comp. Ex. 9 | $V_1Cr_{0.9}B_{0.5}P_{0.3}Mo_{0.1}K_{0.05}$ | 3.03 | 2,6-dichlorotoluene | 90.7 | 80.7 |
| Comp. Ex. 10 | $V_1Cr_{0.9}B_{0.5}P_{0.3}K_{0.1}$ | 2.72 | 2,6-dichlorotoluene | 93.5 | 74.2 |
| Comp. Ex. 11 | $V_1Cr_{0.9}B_{0.5}P_{0.05}Mo_{0.45}K_{0.05}$ | 2.89 | 2,6-dichlorotoluene | 88.6 | 81.2 |

As can be seen from the data shown in Table 2, the various catalysts known in the art are somewhat lacking in versatility and show lower catalytic activity (conversion) and selectivity when used in the reaction of some halogenated aromatic hydrocarbons. In contrast, the catalyst obtained in the working examples of the present application has better universality, and shows good catalytic activity and selectivity in the ammoxidation of various halogenated aromatic hydrocarbons.

In the above description, the concept of the present application has been described with reference to the embodiments. However, it will be understood by those skilled in the art that various modifications and changes can be made without departing from the scope of the present invention defined in the appended claims. Accordingly, the description and drawings should be regarded as illustrative rather than limiting, and all such modifications and changes are covered by the present invention.

It is to be understood that some of the features described separately in a plurality of embodiments for the sake of clarity may also be provided as a combination in a single embodiment. Conversely, a plurality of different features that are described in a single embodiment for the sake of brevity may also be provided separately or in any sub-combination in different embodiments.

The invention claimed is:

1. A catalyst suitable for use as a fluidized-bed catalyst for the production of halogenated aromatic nitriles, comprising an active component and a support, the active component being a complex having the following composition expressed in atomic ratio:

$VP_aCr_bA_cM_dO_x$ wherein:
A represents at least one metal selected from the group consisting of alkali metals and alkaline earth metals;
M represents at least one element selected from the group consisting of Ti, Zr, Hf, La, Ce, Nb, Mo, W, Co, Zn, Fe, Ni, B, Sb, Bi, As, Ga, Ge, Sn and In;
a is in a range of from greater than 0 to 1.5;
b is in a range of 0.1-1;
c is in a range of 0-0.5;
d is in a range of 0-1;
x is the number of oxygen atoms required to satisfy the valence of each element in the active component;
the support being selected from the group consisting of silica and molecular sieves,
wherein in the XRD spectrum of the catalyst, diffraction peaks are present at $2\theta=27.8\pm0.5°$ and $2\theta=13.8\pm0.5°$, and the ratio of the height ($I_1$) of the diffraction peak at $2\theta=27.8\pm0.5°$ to the height ($I_2$) of the diffraction peak at $2\theta=13.8\pm0.5°$, i.e. $I_1:I_2$, is in a range of 3.5-6.

2. The catalyst according to claim 1, wherein a is in a range from 0.5 to 1.5 and c is in a range from 0.01 to 0.5.

3. The catalyst according to claim 1, wherein the support is a pure-silica molecular sieve.

4. The catalyst according to claim 1, wherein the support is a composite support composed of a pure-silica molecular sieve and silica, wherein the weight ratio of the pure-silica molecular sieve to silica is in a range from 1:9 to 9:1.

5. The catalyst according to claim 1, wherein the catalyst can be prepared by a method comprising the steps of:
1) dissolving a vanadium-containing raw material and a chromium-containing raw material in an acid, and mixing the resultant with a solution of a M-containing raw material to obtain a first mixed solution;
2) mixing and reacting a phosphorus-containing raw material, water and a support to obtain a second mixed solution;
3) combining the first mixed solution with the second mixed solution and subjecting the resultant to concentration to obtain a mixed slurry; and
4) drying and calcining the mixed slurry to obtain the final catalyst.

6. The catalyst according to claim 5, wherein the catalyst is prepared by a method comprising the steps of:
1) dissolving an amount of the vanadium-containing raw material and the chromium-containing raw material in a heated acid solution, adding thereto the promoting element-containing raw material(s) other than the phosphorus-containing raw material, respectively, heating and stirring to obtain the first mixed solution;
2) adding the support into an aqueous phosphoric acid solution, and fully heating and stirring to obtain the second mixed solution;
3) slowly adding the first mixed solution to the second mixed solution, stirring and subjecting the resultant to concentration to obtain the mixed slurry with a certain solid content; and
4) drying and molding the mixed slurry to obtain a catalyst precursor, and calcining the catalyst precursor to obtain the final catalyst.

7. The catalyst according to claim 5, wherein the vanadium-containing raw material is selected from the group consisting of vanadium pentoxide, ammonium metavanadate, vanadium sulfate, and vanadium salts of organic acids; the chromium-containing raw material is selected from the group consisting of chromium sesquioxide and compounds that can be converted into chromium oxides by calcining; the acid is selected from oxalic acid; the M-containing raw material is selected from the group consisting of oxides, nitrates or other soluble compounds of M; and the phosphorus-containing raw material is selected from the group consisting of phosphorus pentoxide, phosphomolybdic acid and phosphotungstic acid.

8. A method for preparation of the catalyst according to claim 1 comprising the steps of:
1) dissolving a vanadium-containing raw material and a chromium-containing raw material in an acid, and mixing the resultant with a solution of a M-containing raw material to obtain a first mixed solution;
2) mixing and reacting a phosphorus-containing raw material, water and a support to obtain a second mixed solution;
3) combining the first mixed solution with the second mixed solution and subjecting the resultant to concentration to obtain a mixed slurry; and
4) drying and calcining the mixed slurry to obtain the final catalyst.

9. The method according to claim 8, further comprising the steps of:
1) dissolving an amount of the vanadium-containing raw material and the chromium-containing raw material in a heated acid solution, adding thereto the promoting element-containing raw material(s) other than the phosphorus-containing raw material, respectively, heating and stirring to obtain the first mixed solution;
2) adding the support into an aqueous phosphoric acid solution, and fully heating and stirring to obtain the second mixed solution;
3) slowly adding the first mixed solution to the second mixed solution, stirring and subjecting the resultant to concentration to obtain the mixed slurry with a certain solid content; and
4) drying and molding the mixed slurry to obtain a catalyst precursor, and calcining the catalyst precursor to obtain the final catalyst.

10. The method according to claim 8, wherein, in the catalyst, a is in a range from 0.5 to 1.5 and c is in a range from 0.01 to 0.5.

11. The method according to claim 8, wherein, in the catalyst, the support is a pure-silica molecular sieve.

12. The method according to claim 8, wherein, in the catalyst, the support is a composite support composed of a pure-silica molecular sieve and silica, wherein the weight ratio of the pure-silica molecular sieve to silica is in a range from 1:9 to 9:1.

13. The method according to claim 8, wherein the vanadium-containing raw material is selected from the group consisting of vanadium pentoxide, ammonium metavanadate, vanadium sulfate, and vanadium salts of organic acids; the chromium-containing raw material is selected from the group consisting of chromium sesquioxide and compounds that can be converted into chromium oxides by calcining; the acid is selected from oxalic acid; the M-containing raw material is selected from the group consisting of oxides, nitrates or other soluble compounds of M; and the phosphorus-containing raw material is selected from the group consisting of phosphorus pentoxide, phosphomolybdic acid and phosphotungstic acid.

14. A method for production of halogenated aromatic nitriles, comprising the step of contacting and reacting a halogenated aromatic hydrocarbon with the catalyst according to claim 1.

15. The method according to claim 14, wherein the contacting and reacting are conducted in the absence of bromoethane.

16. The catalyst according to claim 1, wherein A represents at least one metal selected from alkali metals.

17. The catalyst according to claim 1, wherein a is in a range from 0.5 to 1, b is in a range from 0.1 to 0.7, c is in a range from 0.01 to 0.3, and d is in a range from 0.01 to 0.5.

18. The catalyst according to claim 3, wherein the pure-silica molecular sieve is one or more selected from the group consisting of MCM-41, MCM-48, SBA-1, SBA-2, SBA-15, SBA-16, MSU, Silicate-1, SSZ-13 and HMS.

19. The catalyst according to claim 4, wherein the weight ratio of the pure-silica molecular sieve to silica is in a range from 1:4 to 4:1; and the pure-silica molecular sieve in the composite support is SSZ-13 molecular sieve.

20. The catalyst according to claim 6, wherein the catalyst precursor obtained in the step 4) is firstly pre-calcined at 300-350° C., and then calcined and activated at 500-700° C. to obtain the final catalyst.

21. The catalyst according to claim 1, wherein a is in a range from 0.5 to 1.5.

22. The method according to claim 8, wherein, in the catalyst, a is in a range from 0.5 to 1.5.

23. The method according to claim 8, wherein, in the catalyst, a is in a range from 0.5 to 1, b is in a range from 0.1 to 0.7, c is in a range from 0.01 to 0.3, and d is in a range from 0.01 to 0.5.

* * * * *